United States Patent

Rakhit

[11] 4,029,810
[45] June 14, 1977

[54] LACTONE ESTERS OF PHENOXYISOBUTYRIC ACIDS

[75] Inventor: Sumanas Rakhit, Dollard des Ormeaux, Canada

[73] Assignee: American Home Products Corporation, New York, N.Y.

[22] Filed: Jan. 2, 1976

[21] Appl. No.: 646,211

[52] U.S. Cl. .................. 424/279; 260/343.3 R; 260/343.6
[51] Int. Cl.² .............. C07D 307/32; C07D 307/83
[58] Field of Search .............. 260/343.3, 343.6; 424/279

[56] References Cited

OTHER PUBLICATIONS

Buehler et al., Survey of Organic Syntheses, Wiley – Interscience, 1970, pp. 817–818.

*Primary Examiner*—Lorraine A. Weinberger
*Assistant Examiner*—Jane T. Fan
*Attorney, Agent, or Firm*—Arthur E. Wilfond

[57] ABSTRACT

Lactone esters of formula

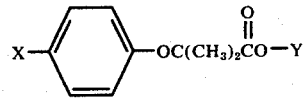

in which X is chloro, bromo or lower alkyl and Y is

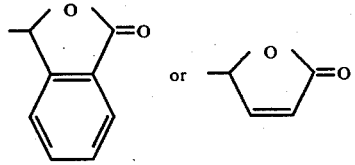

are disclosed. The lactone esters possess antihyperlipoproteinemic activity. Methods for the preparation and use, as well as pharmaceutical compositions of the lactone esters, also are disclosed.

6 Claims, No Drawings

LACTONE ESTERS OF PHENOXYISOBUTYRIC ACIDS

BACKGROUND OF THE INVENTION

1. Field of the Invention

This invention relates to lactone esters of phenoxyisobutyric acid having valuable pharmaceutical properties, to a process for preparing the esters, to pharmaceutical preparations thereof, and to a method for their use.

2. Prior Art

The association of excessive plasma concentrations of lipoproteins or of plasma lipids with increased risk of heart attack, stroke, and sudden deaths is well established. Consequently, the consensus of informed opinion is that elevated levels of cholesterol and/or triglycerides should be reduced by appropriate long term therapy.

The generally accepted Frederickson-Levy-Lees classification of lipid disorders based on lipoprotein disturbances lists five catagories, Types I to V, of hyperlipoproteinemia. This classification allows a more rational choice of therapeutic programs for the treatment of hyperlipoproteinemia, see R. I. Levy, Fed. Proc., 30, 829 (1971). Although a variety of drugs are available for the treatment of hyperlipoproteinemia, none of them is adequate for the general treatment of all types of hyperlipoproteinemias. At the present time, the preferred drugs for treating hyperlipoproteinemia are dependent on the classification of the syndrome and are thus specific for each syndrome; for example, see R. S. Lees and D. E. Wilson, New Engl. J. Med., 284, 186 (1971).

The esters of this invention have been found to be effective for reducing levels of cholesterol and triglycerides in the blood of mammals exhibiting hyperlipoproteinemia and associated conditions. The esters are effective at dosages which do not elicit undesirable side effects. Furthermore, the esters are effective for treating hyperlipoproteinemia in general, notably the syndromes comprising hyperlipoproteinemias of Types IIa, IIb, III and IV.

The lactone esters of this invention are prepared by a convenient process from readily available starting materials. Consequently, the esters are inexpensive and readily available.

The esters of this invention feature a combination of chemical subunits; namely, a lactone ester, comprising a 3-oxo-furan-1-yl moiety, associated with a phenoxyisobutyric acid. Esters of phenoxyisobutyric acid are known; for example, lower alkyl esters thereof are described in U.S. Pat. No. 3,262,850, issued July 26, 1966 and 3-pyridylmethyl esters thereof are described in U.S. Pat. No. 3,369,025, issued Feb. 13, 1968. Prior Art compounds are distinguished from the compounds of the present invention in that they lack the novel ester moiety of the compounds of this invention.

SUMMARY OF THE INVENTION

The lactone esters of this invention are represented by formula 1

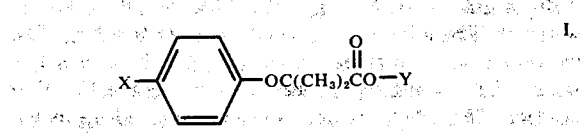

in which X is chloro, bromo or lower alkyl and Y is

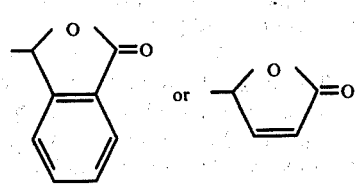

The esters are readily prepared by a process described herein.

Another aspect of the invention relates to pharmaceutical formulations comprising the lactone esters of formula 1 and a pharmaceutically acceptable carrier.

The compounds of formula 1 possess hypocholesterolemic and triglyceride lowering properties and administration of the compounds to hyperlipoproteinemic mammals lowers blood cholesterol and triglyceride concentrations.

DETAILS OF THE INVENTION

The term "hyperlipoproteinemia" as used herein contemplates an increase over normals levels in one or more of the plasma lipoprotein classes and includes conditions wherein the levels of plasma cholesterol, triglycerides or both are increased.

The term "lower alkyl" as used herein contemplates hydrocarbon radicals having one to three carbon atoms and includes methyl, ethyl, isopropyl and propyl.

The hypocholesterolemic and triglyceride lowering properties of the compounds of formula 1 of the present invention are demonstrated in standard pharmacologic tests, for example, in procedures similar to the in vivo tests, described by C. H. Duncan and M. M. Best, Amer. J. Clin. Nutr., 10 297 (1962), and by the general tests described by L. W. Kinsell in "Pharmacologic Techniques in Drug Evaluation", Vol. 2, P. E. Siegler and J. H. Moyer, Eds., Year Book Medical Publishers, Inc., Chicago, 1967, pp. 711–720.

When used as antihyperlipoproteinemic agents, a blood cholesterol and triglyceride lowering amount of the compounds of formula 1 is administered to hyperlipoproteinemic mammals, for example rats, either alone or with pharmaceutically acceptable carriers, the proportion of such carriers being determined by the solubility and chemical nature of the compound, chosen route of administration and standard biological practice. For example, the compounds may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present esters of formula 1 will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in a range of from about 0.1 mg to about 100 mg per kilo per day, although as aforementioned variations will occur. However, a dosage level that is in the range of from about 1.0 mg to about 50 mg per kilo per day is most desirably employed in order to achieve effective results.

PROCESS

A convenient process for preparing the compounds of formula 1 comprises reacting a phenoxyisobutyric acid addition salt of formula 2

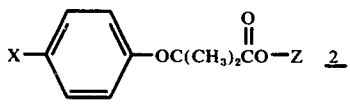

in which X is as defined herein and Z is a metal selected from the group consisting of sodium, potassium, lithium or silver with 0.8 to 2.0 moles, preferably 1.0 mole, of a compound selected from the group consisting of the compounds of formulae 3a and 3b

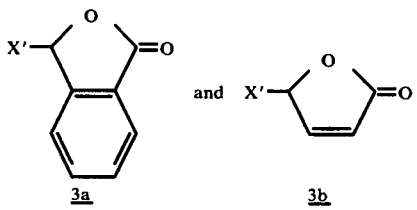

in which $X^1$ is chloro or bromo to give the corresponding compound of formula 1.

The reaction is performed preferably in a polar, aprotic solvent. Examples of suitable solvents include dimethylformamide, dimethyl acetamide, acetonitrile, acetone, hexamethylenetriphosphoramide, tetrahydrofuran and dioxane. Temperatures for the reaction range from 50° to 150° C, preferably 55° to 125° C. The time required to effect the reaction is dependent on the temperature; however, a reaction time ranging from 1 to 24 hours, or more often 2 to 6 hours, usually is sufficient.

Alternatively, the compounds of formula 1 are prepared by reacting a phenoxyisobutyric acid of formula 2 in which X is as defined herein and Z is hydrogen according to the aforementioned conditions in the presence of an excess, preferably 1.0 to 2.0 equivalents, of a suitable base, for example, sodium or potassium carbonate or sodium hydride. Preferred conditions include the use of acetone as the solvent and sodium or potassium carbonate as the base.

The requisite phenoxyisobutyric acids and their addition salts of formula 2 are either known, U.S. Pat. No. 3,558,640, cited above, or are prepared by known methods.

With reference to the requisite compounds of formula 3a, 2-bromophthalide has been described by R. L. Shriner and J. F. Wolf, Organic Synthesis, 23, 74 (1943). Likewise, 2-chlorophthalide is prepared by following the same procedure but replacing bromine with chlorine, respectively. Alternatively, the compounds of formula 3a are prepared by the method of Example 1 of this disclosure.

With reference to the requisite compound of formula 3b, 4-bromo-4-hydroxy-2-butenoic acid γ-lactone (3b, $X^1 = Br$) has been described by S. H. Schroeter, et al., Ann. Chem., 697, 42 (1966). By replacing thionyl bromide with thionyl chloride, the method of Schroeter, et al., for preparing 4-bromo-4-hydroxy-2-butenoic acid γ-lactone is employed to prepare 4-chloro-4-hydroxy-2-butenoic acid γ-lactone.

The following examples illustrate further this invention.

EXAMPLE 1

2-Bromophthalide (3a, $X^1 = Br$)

A suspension of 1.34 g of phthalide and 1.78 g of N-bromo-succinimide in 100 ml of dry carbon tetrachloride is irradiated with an ultraviolet lamp for 30 minutes. The suspension becomes clear and then a precipitation of succinimide occurs. The reaction mixture is cooled and washed with cold, dilute sodium bicarbonate and water. Concentration of the carbon tetrachloride solution affords a solid, which on recrystallization from ether-hexane affords the title compound, mp 75° – 76° C.

In the same manner but replacing N-bromosuccinimide with N-chlorosuccinimide, 2-chlorophthalide is obtained.

EXAMPLE 2

2-(4-Chlorophenoxy)-2-methylpropionic Acid 1,3-Dihydro-3-oxo-2-benzofuran-1-yl Ester (I, X = Cl and

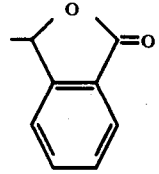

PROCEDURE A

A solution of 236 mg (1.0 mmole) of the sodium salt of 2-(4-chlorophenoxy)-2-methylpropionic acid (the compound of formula 2 in which X is chloro and Z is sodium) and 213 mg (1.0 mmole) of 2-bromophthalide in 10 ml of dimethylformamide is heated at 120° C for 4 hr. The mixture is cooled and poured into ice-water. The resulting mixture is extracted with ethyl acetate. The extract is washed with cold, dilute sodium bicarbonate and water, dried ($Na_2SO_4$), filtered and concentrated. The solid residue is recrystallized from ether-hexane to give the title compound, mp 100° – 101° C.

PROCEDURE B

The sodium salt of 2-(4-chlorophenoxy)-2-methylpropionic acid (1.4 g, 6 mmoles, the compound of formula 2 in which X is chloro and Z is sodium) is dissolved in 50 ml of acetone by adding 1 ml of water. 2-Bromophthalide (1.2 g 6 mmoles) is added to the solution. The mixture is heated at reflux for 3 hr. The mixture is concentrated to ca. 20 ml and poured into water. The resulting mixture is extracted with ethyl acetate. The ethyl acetate extract is worked up in the same manner as described in Procedure A to give the title compound.

By following Procedure A or B but replacing the sodium salt of 2-(4-chlorophenoxy)-2-methylpropionic acid with the corresponding potassium, lithium or silver salt, the title compound is obtained.

The title compound is also obtained by following Procedure A or B of this Example but replacing 2-bromophthalide with 2-chlorophthalide.

By following Procedure A or B but replacing the sodium salt of 2-(4-chlorophenoxy)-2-methylpropionic acid with the sodium, potassium, lithium or silver salt of 2-(4-bromophenoxy)-2-methylpropionic acid or the sodium, potassium, lithium or silver salt of 2-[4-(lower alkylphenoxy)]-2-methylpropionic acid, 2-(4-bromophenoxy)-2-methylpropionic acid 1,3-dihydro-3-oxo-2-benzofuran-1-yl ester and 2-[4-(lower alkylphenoxy)]-2-methylpropionic acid 1,3-dihydro-3-oxo-2-benzofuran-1-yl ester are obtained, respectively.

By following Procedure A or B of this Example and using the appropriate compound of formula 2 but replacing 2-bromophthalide with 4-bromo-4-hydroxy-2-butenoic acid γ-lactone or 4-chloro-4-hydroxy-2-butenoic acid γ-lactone, the corresponding compound of formula 1 in which

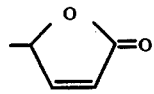

is obtained.

We claim:
1. A compound of formula 1

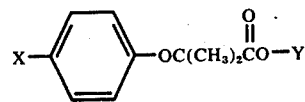

in which X is chloro, bromo or lower alkyl and Y is

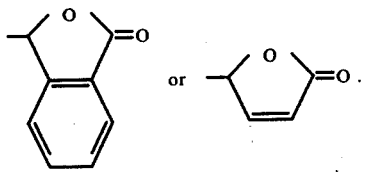

2. 2-(4-Chlorophenoxy)-2-methylpropionic acid 1,3-dihydro-3-oxo-2-benzofuran-1-yl ester, as claimed in claim 1.

3. A method for lowering concentrations of blood cholesterol and triglycerides in mammals in need thereof which comprises administering to said mammal a blood cholesterol and triglyceride lowering amount of a compound of formula 1 as claimed in claim 1.

4. The method of claim 3 in which the compound of formula 1 is 2-(4-chlorophenoxy)-2-methylpropionic acid 1,3-dihydro-3-oxo-2-benzofuran-1-yl ester.

5. A pharmaceutical composition for lowering concentrations of blood cholesterol and triglycerides in mammals in need thereof comprising an effective amount of a compound of formula 1 as claimed in claim 1 and a pharmaceutically acceptable carrier.

6. The pharmaceutical composition of claim 5 in which the compound of formula 1 is 2-(4-chlorophenoxy)-2-methylpropionic acid 1,3-dihydro-3-oxo-2-benzofuran-1-yl ester.

* * * * *